United States Patent
Han et al.

(10) Patent No.: US 10,569,102 B2
(45) Date of Patent: Feb. 25, 2020

(54) SYSTEM AND METHOD FOR INDUCING RESPIRATION

(71) Applicant: Samsung Life Public Welfare Foundation, Seoul (KR)

(72) Inventors: Youngyih Han, Seoul (KR); Hee Chul Park, Seoul (KR); Eun Hyuk Shin, Seoul (KR); Jung Suk Shin, Seoul (KR); Jin Sung Kim, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 30 days.

(21) Appl. No.: 15/509,666

(22) PCT Filed: Oct. 22, 2015

(86) PCT No.: PCT/KR2015/011172
§ 371 (c)(1),
(2) Date: Mar. 8, 2017

(87) PCT Pub. No.: WO2016/064204
PCT Pub. Date: Apr. 28, 2016

(65) Prior Publication Data
US 2017/0281970 A1  Oct. 5, 2017

(30) Foreign Application Priority Data

Oct. 22, 2014  (KR) .................. 10-2014-0143595

(51) Int. Cl.
*A61N 5/10* (2006.01)
*A61M 21/02* (2006.01)
(Continued)

(52) U.S. Cl.
CPC .......... *A61N 5/1037* (2013.01); *A61B 5/0077* (2013.01); *A61B 5/0816* (2013.01);
(Continued)

(58) Field of Classification Search
CPC ................ A61N 5/1037; A61N 5/1068; A61N 5/103–1084
See application file for complete search history.

(56) References Cited

U.S. PATENT DOCUMENTS 4,232,333 A  11/1980  Hiruma et al.
5,825,936 A  10/1998  Clarke et al.
(Continued)

FOREIGN PATENT DOCUMENTS

CN  101422368 A  5/2009
CN  201260669 Y  6/2009
(Continued)

OTHER PUBLICATIONS

International Search Report and Written Opinion issued by the Korean Patent Office, acting as the ISA, for International Application PCT/KR2015/011172 dated Feb. 2, 2016.

*Primary Examiner* — Thaddeus B Cox
(74) *Attorney, Agent, or Firm* — McCarter & English, LLP (57) ABSTRACT

A system for inducing respiration according to one embodiment of the present invention comprises: an imaging unit for picking a respiration image of a patient; a respiration signal conversion unit for obtaining a respiration signal of the patient by image processing, and tracking and analyzing the respiration image of the patient obtained from the imaging unit; and a respiration determination unit for determining one or more of whether the obtained respiration signal is suitable for radiation treatment, whether the obtained respiration signal is stable, and whether a matching score between the respiration signal of the patient and a guide respiration is greater than a predetermined reference value; and a respiration guide unit for providing the respiration
(Continued)

signal of the patient, obtained from the respiration signal conversion unit, together with a stored guide signal.

4 Claims, 7 Drawing Sheets

(51) Int. Cl.
| | |
|---|---|
| *A61B 5/00* | (2006.01) |
| *A61B 5/11* | (2006.01) |
| *A61B 5/113* | (2006.01) |
| *A61B 5/08* | (2006.01) |
| *A61M 21/00* | (2006.01) |

(52) U.S. Cl.
CPC .......... *A61B 5/1128* (2013.01); *A61B 5/1135* (2013.01); *A61B 5/486* (2013.01); *A61B 5/7292* (2013.01); *A61M 21/02* (2013.01); *A61N 5/1038* (2013.01); *A61N 5/1068* (2013.01); *A61B 5/1127* (2013.01); *A61B 2505/05* (2013.01); *A61B 2576/00* (2013.01); *A61M 2021/005* (2013.01); *A61M 2021/0088* (2013.01); *A61M 2230/42* (2013.01)

(56) References Cited

U.S. PATENT DOCUMENTS

| | | | |
|---|---|---|---|
| 6,621,889 | B1 | 9/2003 | Mostafavi |
| 7,899,208 | B2 | 3/2011 | Kondo et al. |
| 7,907,765 | B2 | 3/2011 | Fauver et al. |
| 9,613,272 | B2 | 4/2017 | Kihara et al. |
| 9,633,480 | B2 | 4/2017 | Enomoto et al. |
| 9,675,293 | B2 | 6/2017 | Ooga et al. |
| 9,817,223 | B2 | 11/2017 | Hein |
| 2004/0254492 | A1 | 12/2004 | Zhang et al. |
| 2004/0254773 | A1* | 12/2004 | Zhang .................. A61B 5/1135 703/11 |
| 2005/0201509 | A1 | 9/2005 | Mostafavi et al. |
| 2005/0201510 | A1 | 9/2005 | Mostafavi |
| 2009/0170664 | A1 | 7/2009 | Shirasaki et al. |
| 2010/0063419 | A1 | 3/2010 | Mostafavi et al. |
| 2012/0119115 | A1 | 5/2012 | Iwata |
| 2012/0253178 | A1 | 10/2012 | Mostafavi |
| 2013/0261424 | A1 | 10/2013 | Han et al. |
| 2014/0275704 | A1 | 9/2014 | Zhang et al. |

FOREIGN PATENT DOCUMENTS

| | | |
|---|---|---|
| CN | 102073273 A | 3/2013 |
| CN | 102985137 A | 3/2013 |
| EP | 0 940 158 B1 | 12/2004 |
| JP | 2002-528194 | 9/2002 |
| JP | 2008-154861 A | 7/2008 |
| KR | 10-0740341 B1 | 7/2007 |
| KR | 10-2008-0071197 A | 8/2008 |
| KR | 10-2013-0103394 A | 9/2013 |
| KR | 10-2014-0092050 A | 7/2014 |

\* cited by examiner

SYSTEM AND METHOD FOR INDUCING RESPIRATION

CROSS-REFERENCE TO RELATED APPLICATIONS

This application is the National Stage entry under 35 U.S.C. § 371 of International Application Number PCT/KR2015/011172 filed on Oct. 22, 2015, published on Apr. 28, 2016 under publication number WO 2016/064204 A1, which claims the benefit of priority under 35 U.S.C. § 119 of Korean patent application number 1.0-2014-01.43595 filed Oct. 22, 2014.

TECHNICAL FIELD

Embodiments of the present invention relate to a system and method for inducing respiration, and particularly, to a respiration inducing system and method for inducing regular respiration of a patient during radiation therapy by imaging a guiding signal for respiration and an actual respiration signal of the patient and providing the patient with the image.

BACKGROUND ART

One of important factors that should be considered during four-dimensional radiation therapy or respiratory-gated radiation therapy for a patient is an assumption that the patient's organs move in constant patterns during the radiation therapy. There may be various kinds of movement factors that have an influence on movement of organs of a human. Among these, keeping respiration nearly constant is very important to radiation therapy.

In radiation therapy using medical radiation therapy equipment, it is most important to intensively irradiate tumor cells while minimize radiation dose to surrounding normal tissues. In particular, radiation therapy for a moving organ essentially requires a technique for controlling beams according to variation of geometric movement of tumor that occurs during the radiation therapy.

Several apparatuses are used to achieve prerequisites associated with respiration during the radiation therapy described above. However, since most of the apparatuses use only guiding signals, patients only intuitively breathe as they have practiced without checking their own respiratory status.

To this end, a conventional radiation therapy technique mainly uses a gating method in which a medical radiation machine is controlled to perform therapy using a real-time position management (RPM) system. However, success or failure of the therapy technique depends on stability of the patient's respiration, and also respiratory-gated radiation therapy for a patient having unstable respiration requires a long treatment time. In addition, since the RPM system sets a respiration phase using only a respiration period and applies the respiration phase to the respiratory-gated radiation therapy without considering a respiration pattern or a respiration volume, the RPM system has very low therapeutic accuracy.

In particular, stereotactic body radiation therapy for a moving organ may have a significantly long treatment time and a very high risk of side effects in comparison to conventional radiation therapies. Accordingly, in order to solve this problem, it is also important to educate and to train so that the patient has a stable respiration period and respiration volume.

Also, for radiation therapy patients having diseases associated with their lungs, it is actually very difficult to maintain stable respiration periods and respiration volumes. Accordingly, when respiratory-gated radiation therapy is conducted for patients with lung diseases, radiation should be delivered only when a respiratory status is stable, thus a breathing assistance device is definitely required The aforementioned background is technical information which the inventors have had or obtained in the course of the present invention and thus may not be publicly known before the filing of this application.

DETAILED DESCRIPTION OF THE INVENTION

Technical Problem

Embodiments of the present invention relate to a system for inducing regular respiration of a patient during radiation therapy. The objective of the present invention is to provide a respiration inducing system that may induce regular respiration of a patient by imaging a guiding signal for respiration and an actual respiration signal of the patient and providing the patient with the image.

Technical Solution

An embodiment of the present invention discloses a respiration inducing system including an imaging unit configured to capture a respiration image of a patient; a respiration signal conversion unit configured to acquire a respiration signal of the patient by imaging processing, tracking, and analyzing the respiration image of the patient obtained by the imaging unit; a respiration determination unit configured to determine one or more of whether the acquired respiration signal is suitable for radiation therapy, whether the acquired respiration signal is stable, and whether a matching score between the respiration signal of the patient and guiding respiration is greater than or equal to a predetermined reference value; and a respiration guide unit configured to provide the respiration signal of the patient acquired by the respiration signal conversion and a stored guiding signal together.

In this embodiment, the respiration determination unit may determine whether the acquired respiration signal is suitable for radiation therapy based on the one or more of information regarding the stability of a respiration period (period & variance), stability of respiration amplitude (amplitude & variance), and stability of a respiration pattern (respiratory pattern) of the acquired respiration signals In this embodiment, the respiration determination unit may provide a new respiration pattern as the guiding respiration when a difference between the respiration signal of the patient and the guiding respiration is greater than or equal to the predetermined reference value for a certain period of time.

In this embodiment, the respiration guide unit may acquire the respiration signal of the patient and display the acquired respiration signal in real time to correspond to the guiding signal while displaying the guiding signal through an input/output unit.

In this embodiment, the respiration inducing system may irradiate radiation beams only when the patient's respiration ranges between an upper threshold and a lower threshold.

In this embodiment, the respiration guide unit may create a patient-specific guiding signal based on information regarding one or more of a respiration period, respiration amplitude, and a respiration pattern of the acquired respiration signal.

Another embodiment of the present invention discloses a respiration inducing method including capturing a respiration image of a patient; acquiring a respiration signal of the patient by processing, tracking, and analyzing the captured respiration image of the patient; determining whether the acquired respiration signal is suitable for radiation therapy; determining whether the acquired respiration signal is stably maintained; storing a current respiration signal as a guiding signal when the acquired respiration signal is stably maintained; and guiding the patient's respiration by providing the acquired respiration signal of the patient and the stored guiding signal together.

In this embodiment, the determining of whether the acquired respiration signal is suitable for radiation therapy may include determining whether the acquired respiration signal is suitable for radiation treatment on the basis of information regarding one or more of a respiration period, respiration amplitude, and a respiration pattern of the acquired respiration signal.

In this embodiment, the respiration inducing method may further include providing a new respiration pattern as patient-specific guiding respiration when the acquired respiration signal is not suitable for radiation therapy.

In this embodiment, the guiding of the patient's respiration may include acquiring the respiration signal of the patient and displaying the acquired respiration signal in real time to correspond to the guiding signal while displaying the guiding signal through an input/output unit.

In this embodiment, the respiration inducing method may further include, after the steps are performed during simulation and stored a determined guiding signal, actual radiation therapy is performed, capturing a respiration image of the patient; acquiring a respiration signal of the patient by processing, tracking, and analyzing the respiration image; determining whether a difference between the acquired respiration signal and the guiding signal stored during the simulation is within a predetermined reference value; and irradiate when the difference is within the predetermined reference value.

In this embodiment, the irradiation may include irradiate only when the patient's respiration ranges between an upper threshold and a lower threshold.

The above and other aspects, features, and advantages of the present invention will become apparent from the following description taken in conjunction with the accompanying drawings, claims, and detailed description.

Advantageous Effects of the Invention

According to the present invention, in order to minimize radiation dose to normal tissues and maximize a radiation dose to tumors, it is possible to perform training and guiding respiration so that a patient's respiration can be regular. It is also possible to obtain stability in a radiation therapy process with the respiration inducing system of the present invention using a bio-feedback principle, which enabling a patient to control his or her respiration while the patient directly views his or her movement when stable respiration or movement of the patient is required. That is, since the patient carries out training by viewing his or her respiration and receiving a feedback, it is possible to increase efficiency of radiation therapy.

It is also possible to establish a patient education system for inducing stable and regular respiration during simulation for respiration-gated radiation therapy or actual therapy through the respiration inducing system of the present invention. It is also possible to induce more stable and regular respiration by displaying a feedback signal using a visual device to a patient.

BEST MODE

While the invention is susceptible to various modifications and alternative forms, specific embodiments thereof are shown by way of example in the drawings and will herein be described in detail. Advantages and features of the present invention and implementation methods thereof will be clarified through following embodiments described with reference to the accompanying drawings. However, the present invention is not limited to the following embodiments and may be implemented in various forms. It will be understood that even though the terms "first," "second," etc. may be used herein to describe various components, these components should not be limited by these terms. These components are only used to distinguish one component from another. The singular forms "a," "an," and "the" include the plural form unless the context clearly dictates otherwise. It should be further understood that the terms "comprises" and/or "comprising" used herein specify the presence of stated features or components, but do not preclude the presence or addition of one or more other features or components. Additionally, the sizes of components depicted in the drawings may be exaggerated or reduced for convenience of explanation. For example, since the sizes and thicknesses of components in the drawings are arbitrarily illustrated for convenience of explanation, the following embodiments are not limited thereto.

Hereinafter, embodiments of the present invention will be described in detail with reference to the accompanying drawings, and the same or similar elements are designated with the same numeral references regardless of the numerals in the drawings and their redundant description will be omitted.

Figure 1:
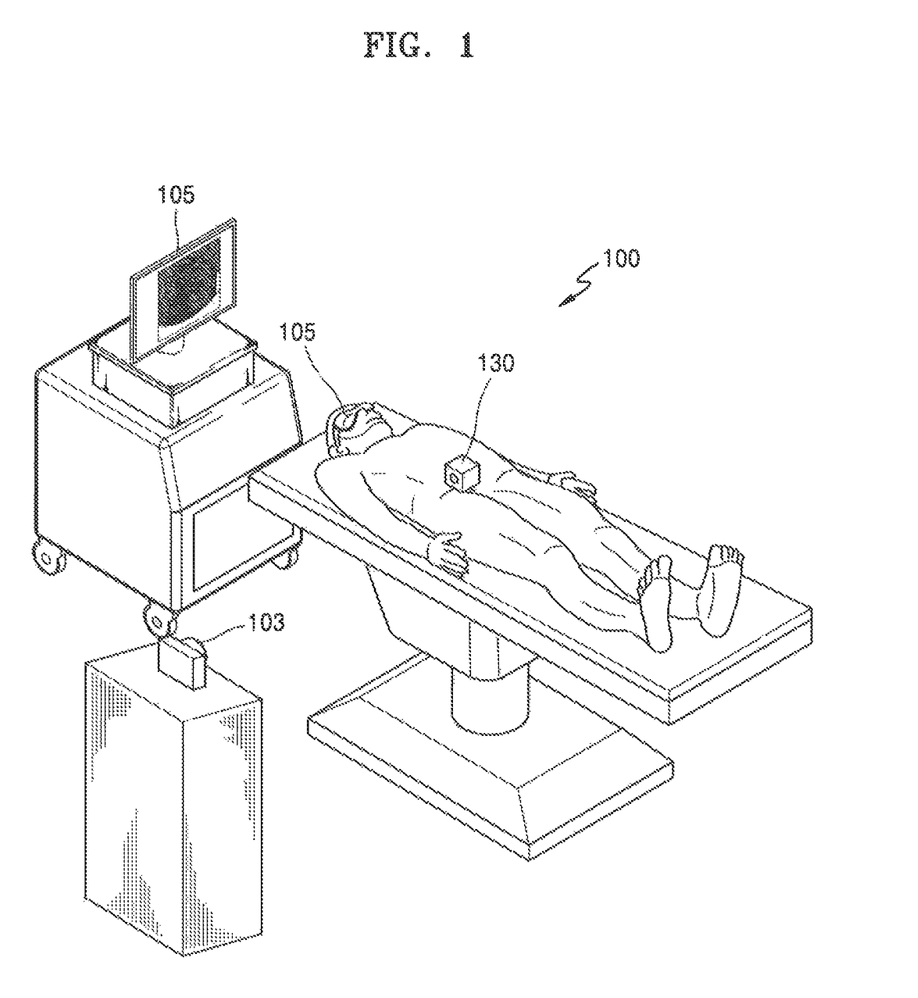
FIG. 1 is a diagram showing a respiration inducing system according to an embodiment of the present invention.
Figure 2:
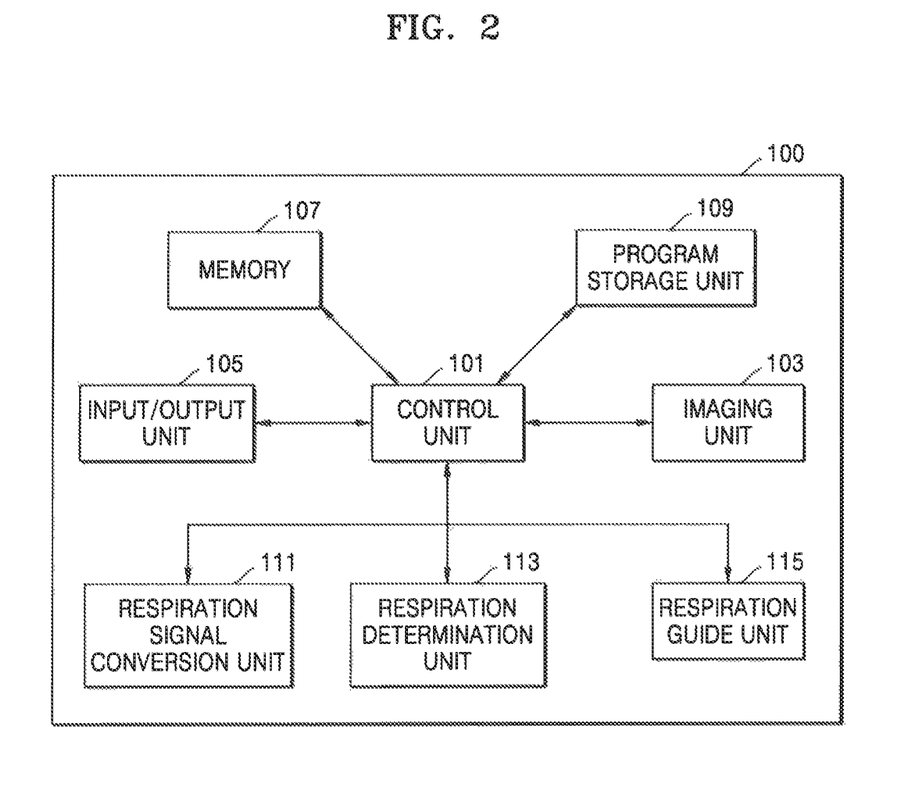
FIG. 2 is a block diagram showing an internal configuration of the respiration inducing system of FIG. 1.

FIG. 1 is a diagram showing a respiration inducing system 100 according to an embodiment of the present invention, and FIG. 2 is a block diagram showing an internal configuration of the respiration inducing system 100 of FIG. 1.

Referring to FIGS. 1 and 2, the respiration inducing system 100 according to an embodiment of the present invention includes a control unit 101, an imaging unit 103, an input/output unit 105, a memory 107, a program storage unit 109, a respiration signal conversion unit 111, a respiration determination unit 113, and a respiration guide unit 115, etc. These will be described in detail below.

In detail, along with development of radiation therapy technique such as stereotaxic radiation surgery, intensity modulated radiation therapy, and image guided radiation therapy, it has become possible to deliver a minimal radiation dose to normal tissues in the vicinity of a target and intensively focus a most radiation dose to a tumor. Meanwhile, radiation therapy for tumors in the liver, lungs, and an abdomen, which are affected by respiration movement, has been continuously increasing.

However, radiation therapy for organs that moves due to respiration, such as the liver and lungs, has limitation in that a radiation dose is not focused on an intended part or is irradiated to an unintended part because precision and accuracy of irradiating technique are reduced due to movement of an organ to be treated. In order to overcome this limitation, a four-dimensional respiratory-gated method is used to perform radiation therapy.

Success or failure of respiratory-gated radiation therapy depends on how well beams are controlled according to variation of geometric movement of an organ that occurs during the radiation therapy. In particular, particle radiation therapy, which has recently been spotlighted, radiation dose distribution is greatly affected by a movement of an organ to be treated in comparison to conventional therapies. Thus, the introduction of the respiratory-gated radiation therapy is essential. The conventional radiation therapy techniques with a linear accelerator use a gating method for tracking movement of tumor only using an external marker. In this method, respiration gating is achieved using a real-time position management (RPM) system.

However, success or failure of this technique depends on stability of respiration of a patient, and also respiratory-gated radiation therapy for a patient having unstable respiration requires a long treatment time. In particular, since stereotactic body radiation therapy and stereotactic radiosurgery have very long treatment times, it is very important to educate and train a patient so that the patient has a regular and stable respiration period and respiration volume during the radiation therapy.

Also, when a treatment plan for the conventional radiation therapy is established static CT images are used. However, due to movement of internal organs caused by respiration of a patient during radiation therapy, actual three-dimensional dose distribution is different from the planned one, and the conventional respiration-gated method partially compensates for this difference. However, when a patient who is undergoing respiratory-gated radiation therapy has irregular respiration, movement caused by the irregular respiration adversely affects the radiation therapy for the moving organs.

In order to solve such a problem, the respiration inducing system 100 according to an embodiment of the present invention provides a system and method for inducing regular respiration of a radiation therapy patient. In detail, the respiration inducing system 100 according to an embodiment of the present invention provides a system and method for controlling a radiation therapy machine in accordance with respiration uniformity of the patient during simulation and actual radiation therapy and enabling the patient to control his or her respiration by showing a guiding signal for respiration together with a feedback signal obtained from the patient Elements of the respiration inducing system 100 of the present invention will be described in detail below.

The control unit 101 is a kind of central processing unit and it controls the entire process of inducing respiration of a patient in the respiration inducing system 100. That is, the control unit 101 drives control software installed in the program storage unit 109, controls the imaging unit 103 to capture a respiration image of a patient, controls the input/output unit 105 to display a guiding signal and a respiration signal of the patient, controls the respiration signal conversion unit 111 to process the respiration image of the patient obtained by the imaging unit 103 and track and analyze the respiration signal, controls the respiration determination unit 113 to determine whether the respiration signal of the patient is suitable for radiation therapy, whether the patient's respiration is stable, and whether a matching score between the respiration signal of the patient and the guiding signal is greater than or equal to a predetermined reference value, and controls the respiration guide unit 115 to provide various services, such as the guiding signal, to the patient so that the patient may maintain stable respiration.

The input/output unit 105 may be configured with a touch recognition display controller or various other input/output controllers. As an example, the touch recognition display controller provides an output interface and an input interface between an apparatus and a user. The touch recognition display controller transmits and receives an electric signal to and from the control unit. Also, the touch recognition display controller displays a visual output to a user, and the visual output may include text, graphics, image, video, and a combination thereof. For example, the input/output unit 105 may be a predetermined display member capable of touch recognition, such as an organic light emitting display (OLED) or a liquid crystal display (LCD). FIG. 1 shows a glasses-type goggle display and a monitor as an example of the input/output unit 105, but is not limited thereto. Various types of display devices, such as a PDA and a smartphone, may be applied.

The memory 107 functions to temporarily store data or the like that is processed by the control unit 101.

The program storage unit 109 has control software that performs a task of capturing a respiration image of a patient and obtaining a respiration signal of the patient from the respiration image, a task of determining whether the patient's respiration is normal, a task of providing a guiding signal to a patient, etc., through the respiration inducing system 100.

Next, elements associated with acquisition, determination, and guiding of the respiration signal will be described in detail.

Figure 6:
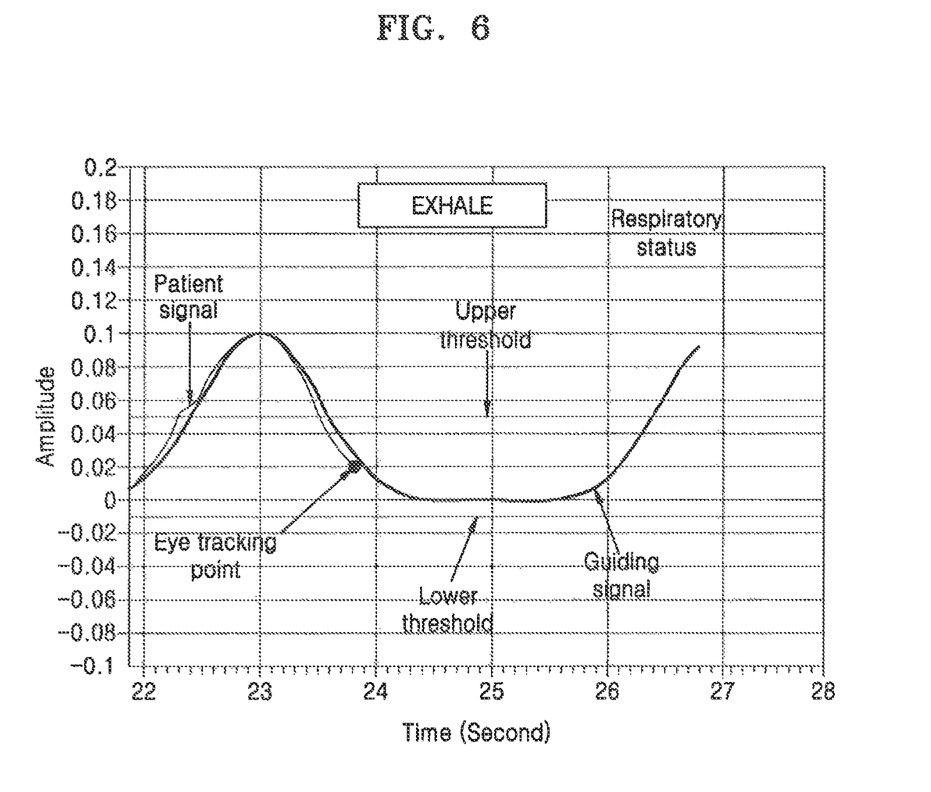
FIG. 6 shows a screen of the respiration inducing system of FIG. 1 on which a guiding signal and a respiration signal of a patient are being displayed.

First, the patient-specific respiration inducing system 100 according to an embodiment of the present invention may be used in simulation that is performed before the respiratory-gated radiation therapy. That is, as shown in FIG. 6, the respiration inducing system 100 provides a patient with a general sinusoidal guiding signal for the purpose of respiration training of the patient during simulation, acquires a patient' respiration image while patient is breathing following the guiding signal through the imaging unit 103, and measures basic parameters associated with the patient respiration such as a respiration period and respiration amplitude from the acquired image. In this case, since a respiration pattern is different for each patient, the respiration inducing system 100 analyzes the measured respiration data and finds an optimal respiration pattern for each patient. In addition, the patient carries out respiration self-training following the pattern which uses the measured and analyzed respiration parameters. Subsequently, after carrying out the respiration training that uses the guiding signal that is found using individual respiration parameters of the patient, the respiration inducing system 100 performs comparison and analyses the measured respiration signal of the patient to determine whether the patient's respiration is stable. In this case, when a matching score between guiding respiration and the patient's actual respiration is less than or equal to a reference value, the respiration inducing system 100 re-analyzes the respiration parameters of an individual patient and re-determines an appropriate respiration inducing signal.

In this case, when it is determined that the patient's respiration is stable, the respiration inducing system 100 provides the patient with an interface for showing the guiding signal and the currently acquired respiration signal of the patient together. In this case, the respiration inducing system 100 provides the patient with a guiding signal that is as similar as possible to the patient's initial respiration so that the patient may breathe regularly while viewing an eye tracking point displayed on the monitor. As described above, the respiration inducing system 100 provides, in real time, the patient with the guiding signal and the respiration signal of the patient acquired through image processing, tracking, and analysis. The acquired respiration signal of the patient is used as basic data for determining whether the respiration is suitable for respiratory-gated radiation therapy in the process of establishing a respiratory-gated radiation therapy plan. When it is determined that the respiration signal is not suitable for respiratory-gated radiation therapy due to a geometrical structure of the tumor and other organs in the process of establishing the therapy plan, for the patient an appropriate respiration parameters is re-established through the simulation for respiration-gated therapy. On the other hand, when it is determined that the respiration signal is appropriate for respiratory-gated radiation therapy respiration, an operator determines an optimal respiratory gating window on the basis of the respiration parameters of the patient provided during the simulation.

The present invention provides a patient with his or her current respiratory status and a patient-specific guiding signal in real time even during respiratory-gated radiation therapy and thus induces regular respiration of the radiation therapy patient. Also, according to the present invention, matching between respiration during the respiratory-gated radiation therapy and respiration during simulation may be analyzed in real time, and also whether the patient's respiration is within the gating window may be continuously observed in real time. When the patient's respiration during the beam delivery in actual therapy is different from that of simulation, or when the patient's respiration is not within the gating window, a beam-off alarm is turned on to inform the operator of an abnormal status of the patient. In this case, the beam is automatically turned off or manually turned off by the operator.

Elements that perform the above roles will be described in detail below.

First, the respiration signal conversion unit 111 acquires a respiration signal by processing, tracking, and analyzing a respiration image of a patient acquired by the imaging unit 103. To this end, a predetermined marker 130 may be put on the patient's chest or abdomen, and the respiration signal conversion unit 111 may process, track, and analyze movement of the marker 130 in the respiration image of the patient acquired by the imaging unit 103. In this case, the respiration signal of the patient (a patient signal) acquired by the respiration signal conversion unit 111 may be displayed on the input/output unit 105 in the form of a sine wave, as shown in FIG. 6.

The respiration determination unit 113 serves to determine whether the respiration signal of the patient is suitable for radiation therapy, whether the patient's respiration is stable, whether a matching score between the patient's respiration and guiding respiration is greater than or equal to a predetermined reference value, etc.

First, the respiration determination unit 113 may determine whether the respiration signal acquired by the respiration signal conversion unit 111 is suitable for radiation therapy. In detail, the respiration determination unit 113 uses a respiration period, respiration amplitude, a respiration pattern, etc. of the acquired respiration signal to determine whether the acquired respiration signal and respiration regularity is suitable for radiation therapy. That is, when the respiration period of the patient is too long or short, or the respiration amplitude of the patient is too large or small, or a respiration pattern of the patient is irregular, the respiration determination unit 113 may determine that the acquired respiration signal is not suitable for respiratory-gated radiation therapy.

Next, the respiration determination unit 113 may determine whether a matching score between the guiding respiration and the respiration signal acquired by the respiration signal conversion unit 111 is greater than or equal to the predetermined reference value. That is, when the difference between the guiding respiration and the patient's respiration is within a certain criterion for a certain time, the respiration determination unit 113 may determine that the patient's respiration is entirely stable and instruct the patient to carry out respiration self-training according to a current guiding respiration pattern even though the patient's respiration is temporarily unstable. On the other hand, when the difference between the guiding respiration and the patient's respiration falls outside the certain criterion for a certain time, the respiration determination unit 113 may determine that stored guiding respiration does not match the patient's respiration and provide a new respiration pattern suitable for an individual patient as the guiding respiration.

Also, the respiration determination unit 113 may determine whether the acquired respiration signal of the patient is stable. That is, the respiration determination unit 113 determines whether the patient's respiration that is initially measured is stably maintained. Also, the respiration determination unit 113 may store a current respiration pattern as a respiration pattern of the patient when the acquired respiration signal is stably maintained and may store a new respiration pattern as the respiration pattern of the patient when the acquired respiration signal is not stable.

The respiration guide unit 115 may serve to provide the guiding signal to the patient so that the patient may maintain stable respiration. That is, by providing the patient with a predetermined sinusoidal guiding signal and the respiration signal of the patient acquired by the respiration signal conversion unit 111 through the input/output unit 105 together, the respiration guide unit 115 may serve to perform guidance such that the patient may adjust his or her respiration according to the guiding signal. FIG. 6 shows a screen in which the respiration guide unit 115 provides the patient with the predetermined sinusoidal guiding signal (the guiding signal) and the respiration signal of the patient (the patient signal) acquired by the respiration signal conversion unit 11 through the input/output unit 105 together. In this case, while displaying the guiding signal (the guiding signal), the respiration guide unit 115 may acquire the respiration signal of the patient and show the acquired respiration signal in real time to correspond to the guiding signal, thus facilitating guidance of the patient's respiration. That is, by moving an eye tracking point according to the respiration signal of the patient, the user may let patient respire according to the eye tracking point and induce stable respiration of the patient.

Mode of the Invention

A respiration inducing method according to an embodiment of the present invention will be described below.

Figure 3A:
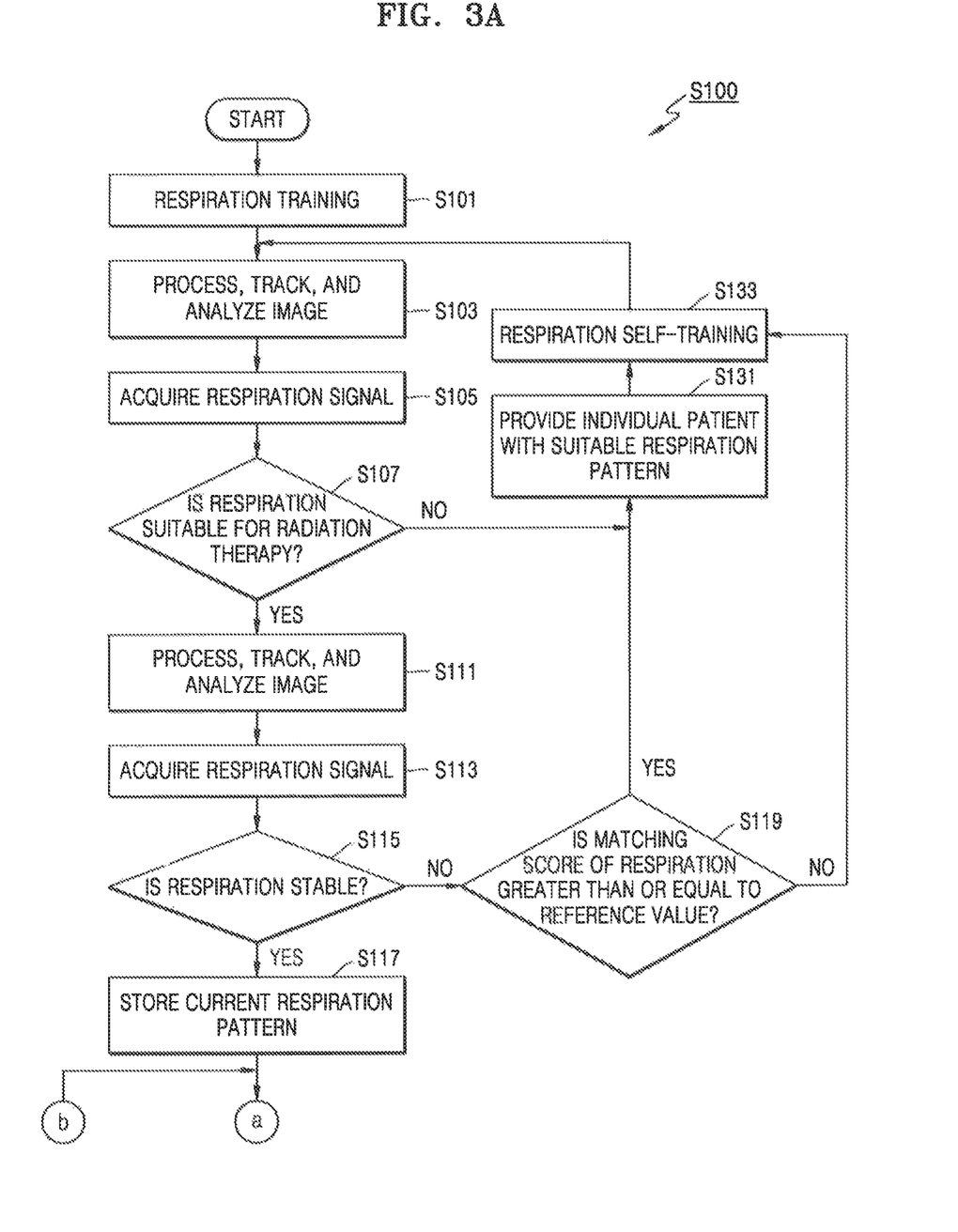
FIGS. 3A and 3B are a flowchart showing a respiration inducing method during simulation using a respiration inducing method according to an embodiment of the present invention.
Figure 3B:
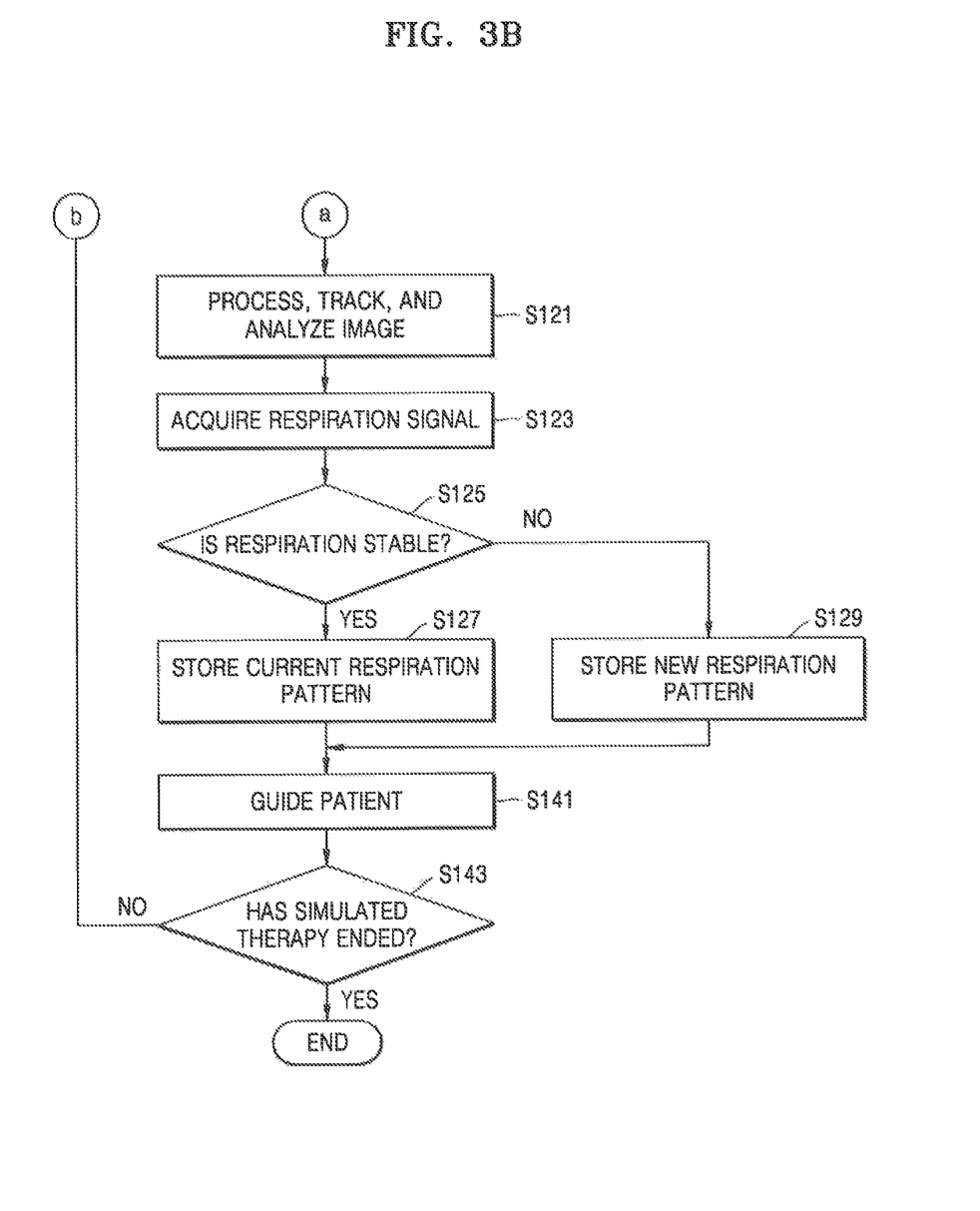

First, in the respiration inducing method according to an embodiment of the present invention, a respiration inducing method during simulation will be described. FIGS. 3A and 3B are a flowchart showing the respiration inducing method during simulation in the respiration inducing method according to an embodiment of the present invention.

Referring to FIGS. 3A and 3B, the respiration inducing method according to an embodiment of the present invention includes carrying out respiratory training by a patient (step S101), processing, tracking, and analyzing a respiration image of the patient acquired by an imaging unit (step S103), acquiring a respiration signal of the patient through the image processing, tracking, and analysis (step S105), determining whether the acquired respiration signal is suitable for radiation therapy (step S107), processing, tracking, and analyzing a respiration image of the patient that is periodically acquired by the imaging unit when the acquired respiration signal is suitable for radiation therapy (step S111), acquiring a respiration signal of the patient through the image processing, tracking, and analysis (step S113), determining whether the acquired respiration signal is stable (step S115), storing a current respiration pattern as a respiration pattern of the patient when the acquired respiration signal is stable (step S117), and determining whether a matching score between guiding respiration and the patient's respiration is greater than or equal to a reference value when the acquired respiration signal is not stable (step S119).

Next, the respiration inducing method includes processing, tracking, and analyzing the respiration image of the patient that is periodically acquired by the imaging unit (step S121), acquiring a respiration signal of the patient through the image processing, tracking, and analysis (step S123), determining whether the acquired respiration signal is stable (step S125), storing the current respiration pattern as the respiration pattern of the patient when the acquired respiration signal is stable (step S127), storing the patient's respiration as a new respiration pattern when the acquired respiration signal is not stable (step S129), guiding the patient with the stored respiration pattern (step S141), and determining whether the simulation has ended and repetitively performing the above steps, starting from step S121, when the simulation has not ended (step S143).

This will be described in detail below.

First, when a patient carries out respiration training (step S101), the respiration signal conversion unit 111 processes, tracks, and analyzes a respiration image of the patient acquired by the imaging unit 103 (step S103) and acquires a respiration signal of the patient (step S105).

Next, the respiration determination unit 113 determines whether the acquired respiration signal is suitable for radiation therapy (step S107). In detail, the respiration determination unit 113 uses a respiration period, respiration amplitude, a respiration pattern, etc. of the acquired respiration signal to determine whether the acquired respiration signal is suitable for radiation therapy. That is, when the respiration period of the patient is too long or short, the respiration amplitude of the patient is too large or small, or the respiration pattern of the patient is irregular, the respiration determination unit 113 may determine that the acquired respiration signal is not suitable for radiation therapy.

When it is determined that the acquired respiration signal is not suitable for radiation therapy, the control unit 101 provides the patient with a new respiration pattern suitable for the patient through the input/output unit 105 (step S131), and the patient carries out respiration self-training (step S133). Then, step S103 to step S107 are repetitively performed.

When it is determined that the acquired respiration signal is suitable for radiation therapy, the control unit 101 processes, tracks, and analyzes a respiration image of the patient that is periodically acquired by the imaging unit 103 (step S111) and acquires a respiration signal of the patient (step S113).

Also, the respiration determination unit 113 determines whether the acquired respiration signal is stable (step S115). That is, the respiration determination unit 113 determines whether the patient's initial respiration that is acquired in an initial stage (step S103 to step S107) is stably maintained.

When the acquired respiration signal is not stable, the respiration determination unit 113 determines whether a matching score between guiding respiration and the patient's respiration is greater than or equal to the reference value (step S119). That is, when the difference between the guiding respiration and the patient's respiration is within a certain criterion for a certain time, the respiration determination unit 113 determines that the patient's respiration is stable on the whole, instructs the patient to carry out respiration self-training according to a current guiding respiration pattern (step S133), and repetitively performs step S103 to step S107 even though the patient's respiration is temporarily unstable. On the other hand, when the difference between the guiding respiration and the patient's respiration is not within the certain criterion for a certain time, the control unit 101 provides the patient with a new respiration pattern suitable for the patient through the input/output unit 105 (step S131), and the patient carries out respiration self-training (step S133). Then, step S103 to step S106 are repetitively performed.

On the other hand, when the acquired respiration signal is stable, the control unit 101 stores a current respiration pattern as the respiration pattern of the patient (step S117).

When the patient carries out respiration training, the respiration signal conversion unit 111 periodically processes, tracks, and analyzes a respiration image of the patient acquired by the imaging unit 103 (step S121) and acquires a respiration signal of the patient through the image processing, tracking, and analysis (step S123).

The respiration determination unit 113 determines whether the acquired respiration signal is stable (step S125). That is, the respiration determination unit 113 determines whether the patient's respiration is stably maintained same as that is initially measured.

When the acquired respiration signal is stable, a current respiration pattern is stored as the respiration pattern of the patient (step S127). On the other hand, when the acquired respiration signal is not stable, a new respiration pattern is stored as the respiration pattern of the patient (step S129).

Last, the patient is guided with the stored respiration pattern (step S141), and it is determined whether the simulation has ended. When the simulation pattern has not ended, the above steps are repetitively performed starting from step S121 (step S143).

Figure 4:
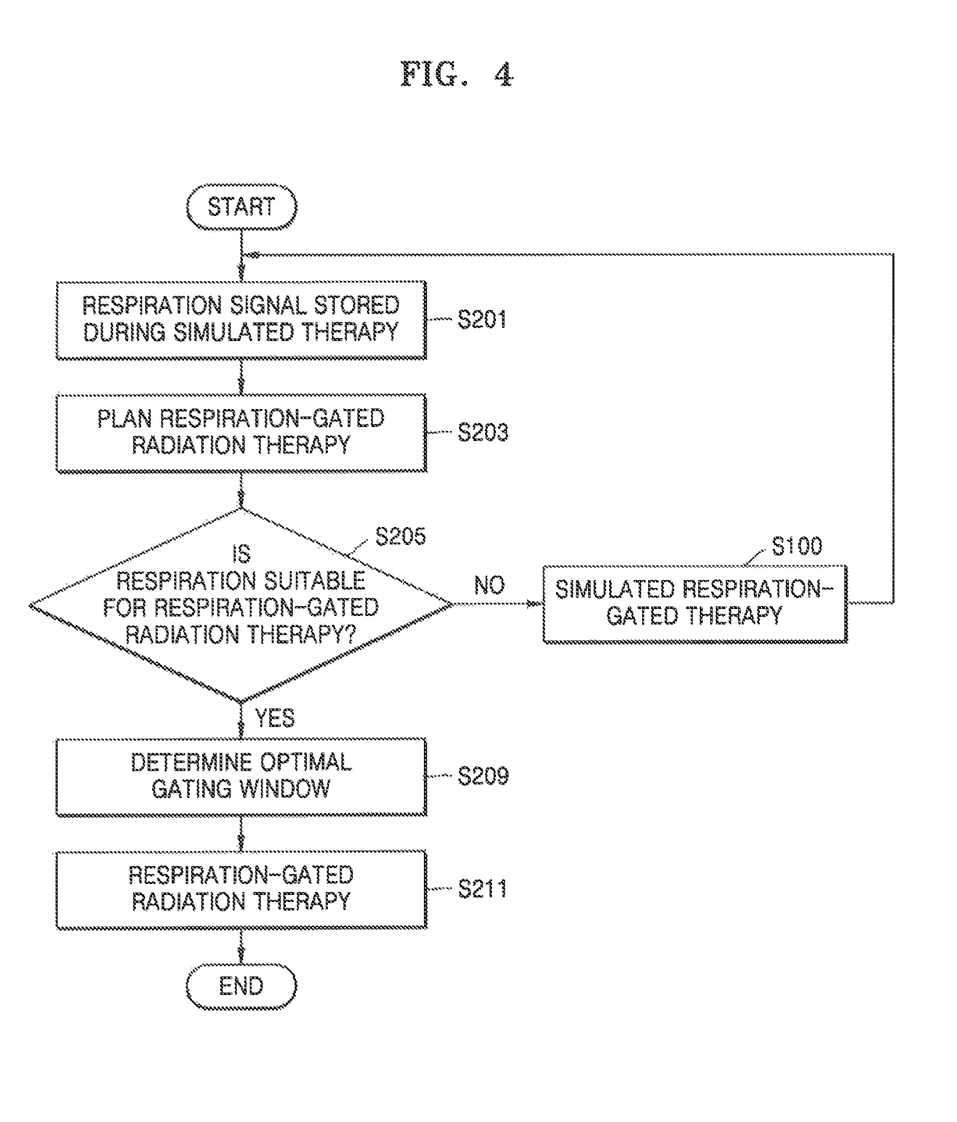
FIG. 4 is a flowchart showing a respiration inducing method during establishment of a radiation therapy plan using a respiration inducing method according to an embodiment of the present invention.

Next, in the respiration inducing method according to an embodiment of the present invention, a respiration inducing method in establishing a radiation therapy plan will be described. FIG. 4 is a flowchart showing the respiration inducing method in the process of establishing a radiation therapy plan using the respiration inducing method according to an embodiment of the present invention.

Referring to FIG. 4, in the respiration inducing method according to an embodiment of the present invention, a respiration inducing method in the process of establishing a radiation therapy plan includes providing a patient with a respiration signal of the patient stored during simulation (step S201), establishing a respiration-gated radiation therapy plan (step S203), acquiring a respiration signal of the patient by processing, tracking, and analyzing a respiration image of the patient acquired by the imaging unit 103, and determining whether the acquired respiration signal is suitable for radiation therapy (step S205), determining an optimal gating window of the patient when the acquired respiration signal is suitable for the radiation therapy (step S207), and performing the respiration-gated radiation therapy (step S209). On the other hand, when the acquired respiration signal is not suitable for the radiation therapy, a suitable respiration pattern of the patient is found by repeating the simulation shown in FIG. 3.

Figure 5:
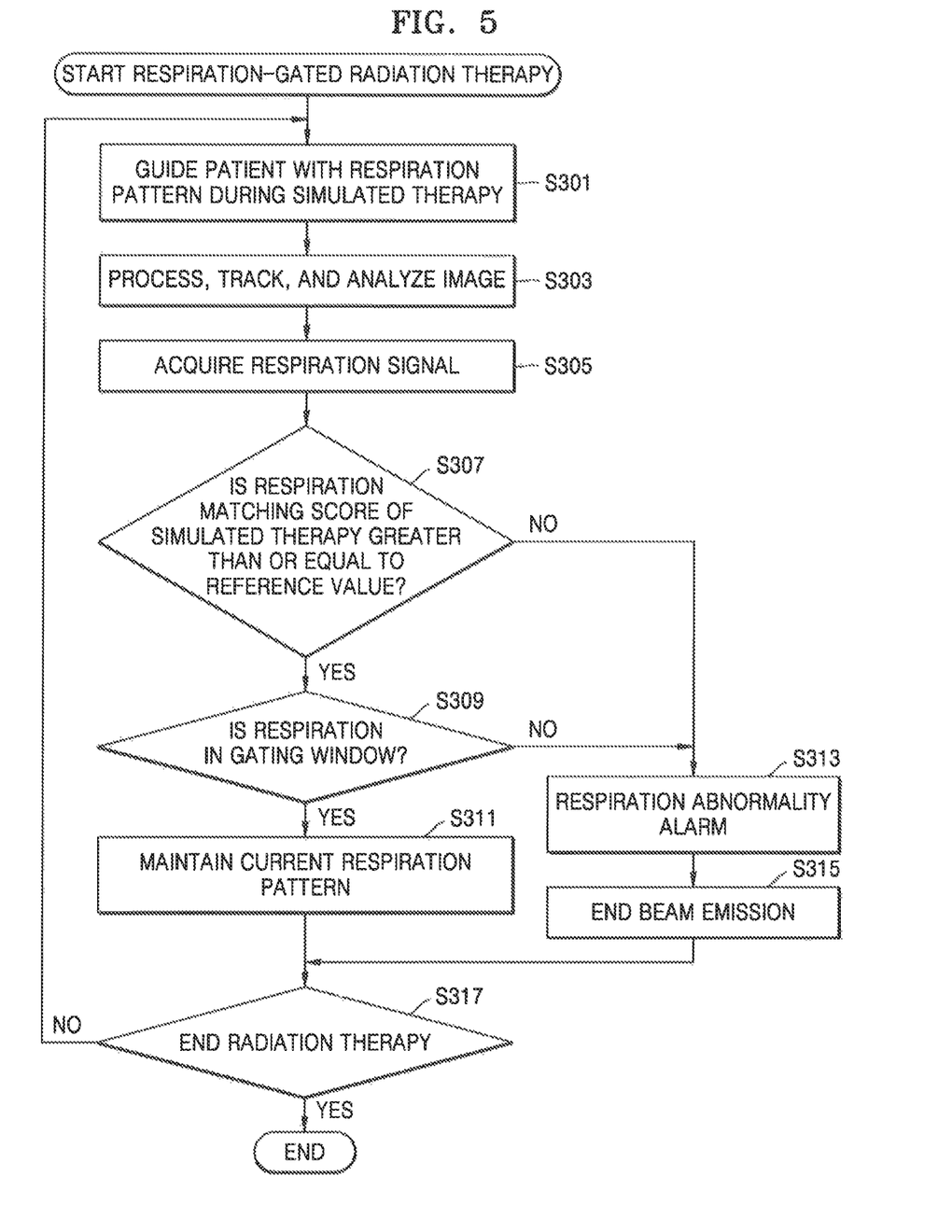
FIG. 5 is a flowchart showing a respiration inducing method during actual radiation therapy using a respiration inducing method according to an embodiment of the present invention.

Next, in the respiration inducing method according to an embodiment of the present invention, a respiration inducing method during actual radiation therapy will be described. FIG. 5 is a flowchart showing the respiration inducing method during actual radiation therapy using the respiration inducing method according to an embodiment of the present invention.

Referring to FIG. 5, in the respiration inducing method according to an embodiment of the present invention, the respiration inducing method during actual therapy includes guiding a patient with a respiration signal of the patient stored during simulation (step S301), processing, tracking, and analyzing a respiration image of the patient acquired by the imaging unit (step S303), acquiring a respiration signal of the patient through the image processing, tracking, and analysis (step S305), determining whether a matching score between the acquired respiration signal and guiding respiration obtained during the simulation is greater than or equal to a reference value (step S307), determining whether the patient respires in the gating window when the matching score is greater than or equal to the reference value (step S309), maintaining a current respiration pattern when the patient respires in the gating window (step S311), and determining whether radiation therapy has ended and repetitively performing the above steps starting from step S301 when the radiation therapy has not ended (step S317). On the other hand, when the matching score is less than or equal to the reference value or when the patient does not respire in the gating window, a respiration abnormality signal is transmitted (step S313), and then radiation beams is stopped. (step S315).

Even though not shown in FIG. 5, control may be performed such that the irradiation is on only when the patient's respiration is within a predetermined range and the irradiation is off when the patient's respiration is not within the predetermined range. That is, referring to FIG. 6, the control is performed such that the irradiation is when the patient's respiration ranges between an upper threshold and a lower threshold and the irradiation is off when the patient's respiration does not range between the upper threshold and the lower threshold.

According to the present invention, it is possible to perform training and guiding so that regularity of the patient's respiration may be obtained in order to minimize a radiation dose to normal tissues and irradiate a maximal radiation dose to tumors.

It is also possible to obtain stability in a radiation therapy process according to the respiration inducing system of the present invention using a bio-feedback principle by allowing a patient to control his or her respiration while the patient directly watch his or her respiration movement when stable respiration of the patient is required. That is, since the patient carries out training by watching his or her respiration and receiving a feedback for the respiration, it is possible to increase efficiency of radiation therapy.

It is also possible to establish a patient education system for inducing stable and regular respiration during simulation for respiration-gated radiation therapy or actual therapy through the respiration inducing system of the present invention. It is also possible to induce more stable and regular respiration by displaying a feedback signal to a patient using a visual device.

The above-described embodiments of the present invention may be implemented in the form of a program instruction that is executable through various computer components and recordable on a computer-readable recording medium. Examples of the computer-readable recording medium may include a magnetic medium such as a hard disk, a floppy disk, or a magnetic tape, an optical medium such as a compact disc-read only memory (CD-ROM) or a digital versatile disc (DVD), a magneto-optical medium such as a floptical disk, and a hardware device such as a ROM, a RAM, or a flash memory that is specially designed to store and execute program instructions. Furthermore, the computer-readable recording medium may include a non-transitory medium that may be transmitted over a network, for example, a medium that is implemented in the form of software or an application and thus transmitted and distributed over a network.

The computer program may be designed and configured specially for the exemplary embodiments or be known and available to those skilled in computer software. Examples of the computer program include a high-level language code executable by a computer with an interpreter in addition to a machine language code made by a compiler.

It should be appreciated that the particular implementations shown and described herein are illustrative of the invention and are not intended to otherwise limit the scope of the present invention in any way. For the sake of brevity, conventional electronics, control systems, software development and other functional aspects of the systems may not haven been described in detail. Furthermore, the connecting lines or connectors shown in the various figures contained herein are intended to represent exemplary functional relationships and/or physical or logical couplings between the various elements. It should be noted that many alternative or additional functional relationships or physical or logical connections may be present in a practical device. Moreover, no element is essential to the practice of the invention unless specifically described herein as "essential" or "critical."

Accordingly, the scope of the invention should be determined by the appended claims and their legal equivalents, rather than by the example given above.

INDUSTRIAL APPLICABILITY

Embodiments of the present invention relate to a system and method for inducing respiration, and may be used in a system and method for inducing regular respiration of a patient since a system for inducing regular respiration of the patient during radiation therapy images a guiding signal for respiration and an actual respiration signal of a patient and provide the image to the patient.

The invention claimed is:

1. A respiration inducing system comprising:
an imaging unit configured to capture a respiration image of a patient;
a respiration signal processing unit configured to acquire a respiration signal of the patient by processing, tracking, and analyzing the respiration image of the patient obtained by the imaging unit;
a respiration signal analyzing unit configured to determine one or more of whether the acquired respiration signal is suitable for radiation therapy, whether the acquired respiration signal is stable, and whether a matching score between the acquired respiration and a guiding signal is greater than or equal to a predetermined reference value; and
a respiration guide unit configured to provide the acquired respiration signal acquired by the respiration signal processing unit and the guiding signal together,
wherein the respiration signal analyzing unit determines whether the acquired respiration signal is suitable for radiation therapy based on information regarding one or more of a respiration period, respiration amplitude, and a respiration pattern of the acquired respiration signal, and
wherein, while the guiding signal is displayed on an input/output unit, the respiration guide unit acquires the acquired respiration signal and displays the acquired respiration signal in real time corresponding to the guiding signal, along with an eye tracking point that moves in real time along the acquired respiration signal, and
wherein the respiration signal analyzing unit is configured to:
determine whether the acquired respiration signal is stably maintained;
store a current respiration signal as the guiding signal when the acquired respiration signal is stably maintained;
determine whether the matching score between the guiding signal and the respiration of the patient is greater than or equal to a reference value when the acquired respiration signal is not stable;
maintain a current guide respiration pattern when a difference between the guiding signal and the acquired respiration signal during a predetermined time is within a predetermined reference as a result of the determining of whether the matching score is greater than or equal to the reference value; and
provide a new respiration pattern to the patient difference between the guiding signal and the acquired respiration signal during the predetermined time is not within the predetermined reference as the result of the determining of whether the matching score is greater than or equal to the reference value.

2. The respiration inducing system of claim 1, wherein the respiration signal analyzing unit provides a new respiration pattern as the guiding signal when the difference between the acquired respiration signal and the guiding signal is greater than or equal to the predetermined reference value for a certain time.

3. The respiration inducing system of claim 1, wherein irradiation is on only when the patient's respiration ranges between an upper threshold and a lower threshold.

4. The respiration inducing system of claim 1, wherein the respiration guide unit creates a patient-specific guiding signal based on information regarding one or more of a respiration period, respiration amplitude, and a respiration pattern of the acquired respiration signal.

* * * * *